United States Patent
Török et al.

(12)

(10) Patent No.: US 6,245,025 B1
(45) Date of Patent: Jun. 12, 2001

(54) METHOD AND APPARATUS FOR MEASURING FETAL HEART RATE AND AN ELECTROACOUSTIC SENSOR FOR RECEIVING FETAL HEART SOUNDS

(76) Inventors: Miklós Török, Komócsy u. 21, H-1141 Budapest; Ferenc Kovács, Vas G. 7, H-1124 Budapest; Sándor Seres, Harmut u. 20/b, H-1105 Budapest; Imre Bartos, Ady E. u. 14, H-2040 Budaors; István Székely, Vág u. 19, H-1133 Budapest; Géza Balog, Lujza. u. 36, H-1086 Budapest; Ákos Herman, Deres. u. 19, H-1124 Budapest, all of (HU)

( * ) Notice: Subject to any disclaimer, the term of this patent is extended or adjusted under 35 U.S.C. 154(b) by 0 days.

(21) Appl. No.: 09/011,840
(22) PCT Filed: Aug. 10, 1995
(86) PCT No.: PCT/HU95/00039
 § 371 Date: Aug. 17, 1998
 § 102(e) Date: Aug. 17, 1998
(87) PCT Pub. No.: WO97/05821
 PCT Pub. Date: Feb. 20, 1997
(51) Int. Cl.[7] ............................................. A61B 5/02
(52) U.S. Cl. ................................... 600/500; 600/511
(58) Field of Search ................................. 600/372, 382, 600/485, 500, 504, 508–509, 511, 528

(56) References Cited

U.S. PATENT DOCUMENTS 4,463,425  7/1984  Hirano et al. .
5,140,992 * 8/1992  Zuckerwar et al. .................. 600/528
5,509,421 * 4/1996  Muller et al. ...................... 600/511 X
5,524,631 * 6/1996  Zahorian et al. .................... 600/511

FOREIGN PATENT DOCUMENTS 1443216  7/1976  (GB) .

* cited by examiner

Primary Examiner—Max Hindenburg
Assistant Examiner—Ryan Carter
(74) Attorney, Agent, or Firm—Kolisch Hartwell Dickinson McCormack & Heuser (57) ABSTRACT

Method and apparatus for long-term, non-invasive measuring of fetal heart rate. The method utilizes the characteristic curves of first and second heart sound received by the preferred electroacoustical converter. The identification and distinction of first and second sounds, furthermore their time relation used for heartbeat identification highly increase the reliability of fetal heart rate determination. The distinction of first and second sound is based on the differences in frequency spectrums measured in a relatively short time window and by the estimation of the power peaks measured on two test frequencies chosen on the two ends of the frequency range of fetal heart sound. The method is implemented in an integrated apparatus to achieve low power consumption for battery-operated long-term measurements. Digital filtering and selective power estimation is applied for continuous computation of power time function on the two test frequencies. The test frequencies can be adaptively modified depending on individual fetal parameters to improve the distinction of the first and second sound. The apparatus is capable to registrate, store and transfer data of fetal heart rate and womb contractions to a personal computer.

31 Claims, 8 Drawing Sheets

METHOD AND APPARATUS FOR MEASURING FETAL HEART RATE AND AN ELECTROACOUSTIC SENSOR FOR RECEIVING FETAL HEART SOUNDS

TECHNICAL FIELD

This invention relates to particularities of monitoring the well-being of a fetus on the basis of fetal heart activity.

BACKGROUND OF THE INVENTION

The widely used CTG equipment for monitoring of fetal heart activity apply ultrasound Doppler technique, where an ultrasonic beam is directed to the fetus, the reflection of which determines the heart movement and hereby fetal heart rate (FHR). However, these equipment are unsuitable for long-time monitoring without inspection, since uncontrolled high-dose exposure may have some harmful effects.

A further technique for this purpose is the phonocardiography (PCG) where acoustic waves excited by heart movement are detected. In the case of fetal heart sounds, however, difficulties arise in the detection and identification of the signals. Acoustic waves of fetal origin reach the sensor placed on the maternal abdomen through a complex transmission path, where significant spectrum variation occurs. Furthermore, disturbances of maternal digestive organs may hinder signal detection. Finally, fetus movements result in the displacement of the optimal sensing point and lead to the decrease of signal level.

An essential advantage of the acoustic method is that the passive manner of the sensing is harmless to the fetus even at very long monitoring time, which makes possible home care. The detection and processing of acoustic signals of fetal heart are dealt with by many researchers.

A fetal monitor is announced in U.S. Pat. No. 2,536,527 to Appel. The invention serves for monitoring fetal condition during delivery. A microphone applied to the stethoscope produces a signal which is amplified, filtered, rectified and used to indicate abnormally high or low FHRs.

U.S. Pat. No. 3,187,098 to Farrar describes a fetal heartbeat detector, which uses a cantilevered piezoelectric crystal mounted within a contacting slab. A fetal monitor is given in U.S. Pat. No. 3,409,737 to Settler et al. This monitor is used with a belt having three microphones. An amplifier is used to selectively amplify the fetal heartbeat and remove the maternal heartbeat.

U.S. Pat. No. 4,781,200 to Baker uses a sensor belt wearing twelve sensors, the detected signal of which are compared to cancel disturbances and trace fetal position. The signal processing is carried out by the conventional FFT method for 128 points applied in every ⅛ seconds, delivering the frequency spectra for selection of coincided components of the sensors. However, because of the relatively long time period of analysis the fast variations in spectral power density are averaged. Thus short time characteristics of frequency components cannot be correctly detected using this method. U.S. Pat. No. 5,140,992 to Zuckerwar et al. uses a belt wearing more piezoelectric polymer film sensors for fetal heartbeat indication.

All of this invention have the common insufficiency that they do not distinguish perfectly the first and second sound and thus they cannot apply this additional information to the identification of fetal heartbeat sound. In addition, a lot of computations are carried out in signal processing, which can be saved without the deterioration of the reliable sound identification. As a consequence, these instruments require high supply current and thus they are for battery operation unsuitable.

Reliable identification of fetal heartbeat is of vital importance at FHR measurement. Consequently, there is need for a solution that enables reliable identification of fetal heartbeats, does not require bulky hardware and allows battery operation even without medical supervision.

GENERAL DISCLOSURE OF THE INVENTION

In a first aspect the aim of the invention is to provide a method for identifying fetal heart sounds with improved reliability. According to a second aspect, the method should be implemented on a low-power electronic circuit to allow designing a portable apparatus suitable for long-term home monitoring. According to a further aspect, the apparatus should enable easy finding of the correct position of the sensor on the maternal abdomen. Advantageously, simultaneous measurement of maternal womb contractions should be possible by using a conventional tocodynameter. According to a further aim of the invention a sensor should be applied that enables improved acoustical detection of fetal heart activity.

The above and other aims can be achieved by the invented method for measuring fetal heart rate on the basis of acoustic signals detected at the maternal abdomen. The invented method comprises the following steps:

converting said acoustic signals into electric signals;

determining power levels $P_a(t)$ and $P_b(t)$ of said signals of fluctuating intensity at test frequencies $f_a$ and $f_b$ being in a lower and higher frequency band of the range of 20 to 80 Hz;

detecting and storing local peak values $P_{a1}$ and $P_{a2}$; as well as $P_{b1}$ and $P_{b2}$ of said power level and relevant times $t_{a1}$ and $t_{a2}$; as well as $t_{b1}$ and $t_{b2}$ for an inspection period $t_s$ following the first one of said detected local peaks;

counting numbers $n_a$ and $n_b$ of said peaks of power levels during said inspection period $t_s$;

storing the value of said power level $P_b(t_{a1})$ when a peak value $P_{a1}$ at said lower test frequency $f_1$ is detected;

determining time differences $dt=t_{a1}-t_{b1}$ and $dt=t_{a2}-t_{b2}$ between detection of first peak values $P_{a1}$ and $P_{b1}$, or $P_{a2}$ and $P_{b2}$ within said inspection period;

classifying detected peaks on the basis of numbers $n_a$, $n_b$, values and timing of said peaks of power levels, and identifying peaks meeting preset criteria as first and second sounds, respectively;

measuring the time difference between an identified first sound and a subsequent second sound representing the closing time;

identifying said first and second peak as a matching pair of sounds of a heartbeat if said closing time is in the range of 140 to 220 ms; and calculating fetal heart rate from a time difference between two consecutively identified heartbeats.

Figure 3A:
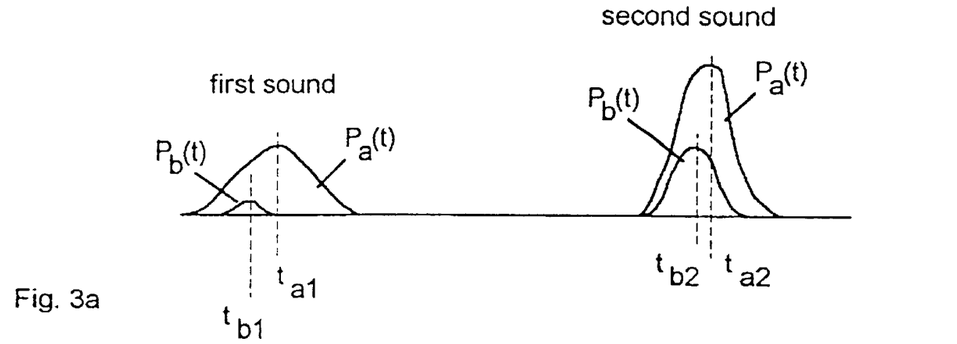
FIG. 3 shows four typical time functions of heartbeat sound power densities calculated at frequencies $f_a$=30 Hz and $f_b$=60 Hz.
Figure 3B:
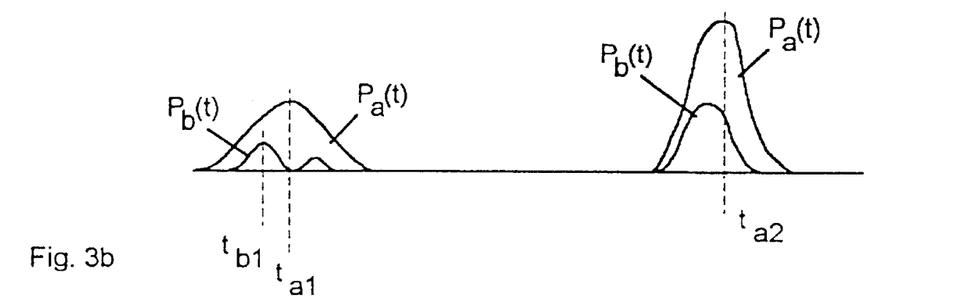
Figure 3C:
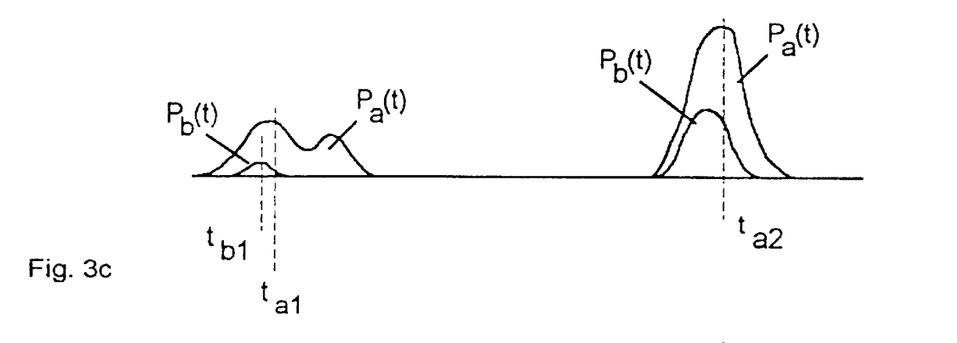
Figure 3D:
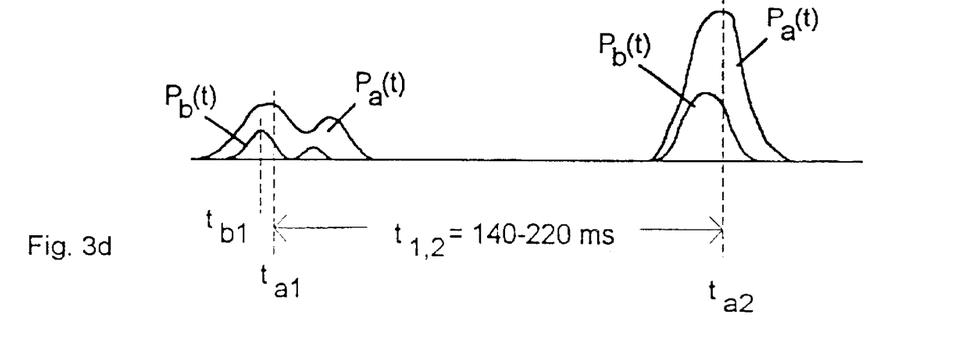

The detected peaks are classified on the basis of the following criteria:

if one local peak is detected on power level $P_a(t)$ as well on power level $P_b(t)$, that means $n_a=1$ and $n_b=1$, and for the time difference $dt=t_{a2}-t_{b2}$ between the two peaks the criterion $-15$ ms$<(t_{a2}-t_{b2})<15$ ms is satisfied, then the detected peak is a second sound (see FIG. 3a, right side), if one local peak is detected on power level $P_a(t)$ as well on power level $P_b(t)$, that means $n_a=1$ and $n_b=1$, and for the time difference $dt=t_{a1}-t_{b1}$ between the two peaks 15 ms<dt<40 ms, furthermore, for the power level $P_b(t)$ the $P_b(t_{a1})/P_b(t_{b1})<0.3$ criterion is satisfied, then the detected peak is a first sound (see FIG. 3a, left side), if one local peak is detected on power level $P_a(t)$ and two peaks on power level $P_b(t)$, that means $n_a=1$ and $n_b=2$, and for the peak values on the power level $P_b(t)$ the $P_b(t_{a1})/P_b(t_{b1})<0.3$ criterion is satisfied, then the detected peak is a first sound (see FIG. 3b), if two local peaks is detected on power level $P_a(t)$ and one peak on power level $P_b(t)$, that means $n_a=2$ and $n_b=1$, and for time difference $dt=t_{a1}-t_{b1}$ between the two peaks the criterion $-15$ ms$<(t_{a2}-t_{b2})<15$ ms is satisfied, then the detected peak is a first sound (see FIG. 3c), if two local peaks is detected on power level $P_a(t)$ as well on power level $P_b(t)$, that means $n_a=2$ and $n_b=2$, then the detected peak is a first sound (see FIG. 3d), Peaks not meeting criteria are classified as undefined sounds. This kind of classification enables identification of heart sounds with an improved reliability. Further criteria, especially for non-typical cases can also be of use. Preferably, said estimation of power $P_a(t)$ at said lower test frequency fa comprises averaging for a time window of 30 to 90 ms; said estimation of power level $P_b(t)$ at said higher test frequency $f_b$ comprises averaging for a time window of 20 to 60 ms. By this measure generally more than one and less than three periods of the sound signal can be evaluated.

Local peak values $P_{a1}$ and $P_{a2}$; as well as $P_{b1}$ and $P_{b2}$ of power levels $P_a$ and $P_b$ are accepted preferably only if their values are exceeding the 1/10 part of the average of previously detected peak values. Thereby noises and interferences have less influence on the reliability of FHR values. Preferably, said lower testing frequency is selected within range 25 to 35 Hz and said upper testing frequency within range 55 to 65 Hz. Thereby a sufficient distinction can be established between said first and second sounds. Other frequency ranges can also be involved to gain additional information.

Test frequencies $f_a$ and $f_b$ can be predetermined by considering weeks of gestation and estimated weight of the fetus, and these can be applied as starting values at the beginning of the measurement. The actual values of said test frequencies can be continuously adjusted on the course of measurements to obtain maximum values for said local peaks of said signal power.

Generally, said inspection time $t_s$ is longer than 80 ms and shorter than 120 ms. However, said inspection time is shortened, if identification of said first sound or said second sound is completed. The closing time usually longer than 140 ms and shorter than 220 ms, but it can be continuously adjusted depending on previously measured values.

In a second aspect the invention relates to an apparatus for implementing the above method. The invented apparatus comprises:

an acoustic sensor for sensing acoustic vibrations deriving from a fetus, said sensor adapted to be placed onto maternal abdomen;

an analog unit for amplifying and enhancing frequencies characteristic to the fetal heart activity, an amplifier having adjustable gain for adjusting the signal level to be in an evaluation range;

an analog to digital converter converting analogous signals to digital samples and connected to said amplifier;

a frequency selective power estimation unit for determining signal level at a lower test frequency $f_a$ within a frequency range from 25 to 35 Hz;

a frequency selective power estimation unit for determining signal level at a higher test frequency $f_b$ within a frequency range from 55 to 65 Hz;

a first and a second peak detector for monitoring said signal levels fluctuating in time and estimated by said first and second power estimation units and establishing occurrence of local peaks of said signal levels;

an identification unit for identifying first and second sounds based upon time, values and sequence of said local peaks;

a computing means for computing fetal heart rate from said identified first and second sounds;

a storage means for storing computed fetal heart rate values;

a communication port for making said stored fetal heart rate values accessible for further evaluation.

Said analog unit preferably comprises an active filter connected to said sensor, said amplifier being connected to said active filter and a sound unit connected to said amplifier for amplifying, filtering and frequency transponding of the input signal. Thereby low frequency signals of high amplitude can be filtered out in order to avoid overdrive of subsequent units.

The apparatus can be designed to contain a conventional microcontroller comprising analog to digital converters, memories, input/output ports and different dedicated units. Said microcontroller can be used for sound identification or for realization of said frequency selective power estimation units and said peak detectors.

According to another possibility, at least one of said frequency selective power estimation units and said peak detectors are comprised in an application specific processor that is connected to said microcontroller. Said application specific processor can be realized conventionally or in integrated form on a silicon chip. This application specific processor can comprise also a gain control circuit connected to the gain control input of said amplifier. The integrated application specific processor allows substantial reduction of supply current and prolonged battery operation.

The apparatus can be completed with a tocodynameter for continuous measurement of womb contractions. Particularly for battery operation the apparatus should comprise a non-volatile memory connected said microcontroller for storing measured fetal heart rate values and additional data provided by said tocodynameter. Thereby these data will remain even if the battery is discharged.

To display of measured data and allow further evaluation the apparatus preferably comprises a serial communication port connected to the microcontroller for connecting said apparatus to a computer via a standard serial communication line.

To indicate subjective feeling of fetal movement and other additional events the apparatus can further comprise an input device, e.g. in form of several pushbuttons that are connected to said microcontroller. To indicate amplifier overdrive and extremely low input signal level the apparatus can comprise light emitting diodes connected to said microcontroller.

Said frequency selective power estimation units can be designed to comprise a digital filter selecting frequencies within said frequency range and a power estimation unit connected to the output of said digital filter. Said digital filter advantageously comprises a register file having serial-in, parallel-out structure and containing the actual input data and number M preceding data to be considered at digital filtering;

a segmented decoder consisting of decoder segments for separately decoding parallel outputs of said register file;

a segmented look-up table storing words to be designated separately by said segmented decoder consisting products $a_k d_{n-k}$, where n is the number of sampling, $d_{n-k}$ is the (n−k)th sampled input data, $a_k$ are filter coefficients with k being in the range of k=0 to M, where M is the order of the filter;

a register file having serial-in, parallel-out structure and containing number N words of filters data;

a second segmented decoder consisting of decoder segments for separately decoding parallel outputs of said register file;

a second segmented look-up table storing words to be designated separately by said segmented decoder consisting products $b_k y_{n-k}$, where $y_{n-k}$ are (n−k)th previous filtered data, $b_k$ are filter coefficients with k being in the range of k=1 to N, where N is the order of the filter, and the meaning of other designations are the same as above;

a summator for consecutively reading out and summing each designed word of said look-up table segments according to the following formula:

$$y_n = \sum_{k=0}^{M} a_k d_{n-k} + \sum_{k=1}^{N} b_k y_{n-k},$$

wherein $y_n$ value is the actual filtered data, and the meaning of other designations are the same as above. This structure of the digital filter requires minimal supply current.

In a preferred form said power estimator comprises a decoder decoding filtered data as an address;

a look-up table addressed by said decoder and containing square values of said addresses;

a summator connected to said look-up table and summing values consecutively read out of said table;

a scanner controlling repetitive and consecutive addressing and summing said square values by said summator;

a second register file connected to said summator and having serial-in, parallel-out structure and containing new summed data in its upper register and oldest in its lowest register;

a replacer having a first input connected to the upper register of said second register file a second input connected to lowest register of register file a third input connected to a third register file, said replacer adapted to adding actual value at its first input to and subtracting actual value at its second input from the value received from said third register file;

a third register file connected to an output of said replacer and having a serial-in, parallel-out structure storing calculated power values and shifting its contents down every step and having parallel outputs, the first of them connected to said third input of said replacer and all connected to a peak detector and adapted to transfer contents to said microcontroller. Said scanner controls power averaging for more steps. This structure minimizes supply current.

Second sounds can be evaluated more advantageously by a frequency selective power estimator unit having another structure. Accordingly, said second frequency selective power estimator unit comprises a register file having a serial-in, parallel-out structure and storing input data $d_i$ measured in a time window;

a decoder decoding data $d_i$ stored in register file and designating corresponding words of a look-up table;

a look-up table containing products according to the following formulae:

$V_i = d_i * \sin(2\pi f_b i / n_{wb}) * Ba(i);$ $W_i = d_i * \cos(2\pi f_b i / n_{wb}) * Ba(i);$ where $d_i$ is the ith data sampled and digitized from the unfiltered signal, $n_{wb}$ is the size of window in number of sample times, and $Ba(i)$ stands for the triangular correction function of Bartlett window;

a look-up table connected to summators and containing squared values as words having a length equal to the word length of said summators;

a summator summing words of said look-up table designated by said decoder to provide an intermediate sum $$S_v = \sum_{i=0}^{n_{wb}} V_i;$$

where $S_v$ is an intermediate sum, and squaring this sum by using look-up table for providing square intermediate sum of $S_v^2$;

a further summator summing words of said look-up table designated by said decoder to provide a second intermediate sum $$S_w = \sum_{i=0}^{n_{wb}} W_i;$$

where $S_w$ is a further intermediate sum, and squaring this sum by using look-up table for providing squared intermediate sum of $S_w^2$;

an adder adding squared intermediate sums for providing a power value at a second test frequency $P_b = (S_v^2 + S_w^2)/n_{wb}$, were $P_b$ is the power in the actual time window for frequency $f_b$;

a register file having a serial-in, parallel-out structure and storing last five sums of adder;

a peak detector for indicating peak values of said power $P_b$.

The above structure needs minimal supply current which can be further decreased if said decoders and summator are adapted to be turned on in sleep mode to reduce power consumption when no heartbeat is expected.

A preferred arrangement of said peak detector comprise comparators connected to parallel outputs of a corresponding register file and an AND gate is connected to outputs of said comparators. The output of this AND-gate indicates occurrences of local peaks of the corresponding power level $P_a$ or $P_b$ by a logical high state.

If monitoring is carried out for a longer time the sound produced by said sound unit may be disturbing and requires extra supply current. To avoid this a switch is provided for to turn off audible heart sounds.

If no personal computer is available a hardcopy of measured data can be produced by simply connecting a printer to said serial communication port that is adapted to be connected to a conventional line printer, Another way of accessing measured data to use a standardized modem adapted to transfer data for telemetric measurements. This modem is linked to microcontroller via said communication port.

According to said third aspect the invention relates to an acoustic sensor for sensing acoustic vibrations deriving from a fetus, said sensor adapted to be placed onto maternal abdomen. This sensor is adapted particularly for use with the apparatus according to the above apparatus and comprises a hollow body and an electroacoustic converter located inside said hollow body and having a sensitive membrane. Said hollow body is partitioned by walls into a first, a second and a third chamber, Said first chamber is open at one side, and is coupled to said second chamber via an opening. Said first chamber has a boring on its sidewall and communicating with the atmosphere. Said second chamber has an upper partition wall formed by a sensitive membrane of an electroacoustic converter. Said third chamber is communicating with the atmosphere through a boring formed in the sidewall of said hollow body.

In a preferred embodiment the sensor said electroacoustic converter is an electrodynamic microphone having an elastic membrane. To achieve reliable contact between said acoustic sensor and the skin of maternal abdomen an elastic ring is provided at the periphery of said open side of said first chamber.

The present invention provides a method to distinguish reliably first and second sounds of fetal heartbeats and an apparatus carrying out this method. The distinction of the two sounds increases significantly the reliability of heartbeat identification and results in correct fetal heart rate values even at high level of disturbances. The method is implemented in a low-power portable equipment, which allows long-time FHR measurements and data registration. Low power consumption is achieved by the utilization of an application specific processor optimized for minimum number of operations.

BRIEF DESCRIPTION OF THE DRAWINGS

Further aims, advantages and features of the invention will be discussed with reference to a preferred embodiment of the invention that is illustrated in the accompanying drawings. In the drawing.

DETAILED DESCRIPTION OF THE PREFERRED EMBODIMENT

Figure 1:
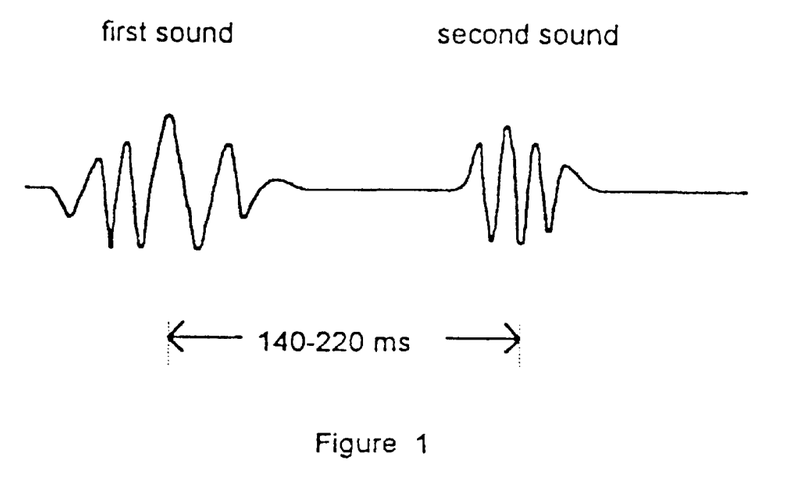
FIG. 1 shows time function of a pair of sound burst caused by a fetal heartbeat.

FIG. 1 shows the time function of the substantially noiseless sound of a fetal heartbeat, where the first sound is related to the contraction, the second one to the relaxation of the heart. Closing time means the time interval between these sound. The signal shown in the figure does not contain components below 25 Hz that were high-pass filtered to depress the low-frequency disturbances.

Figure 2:
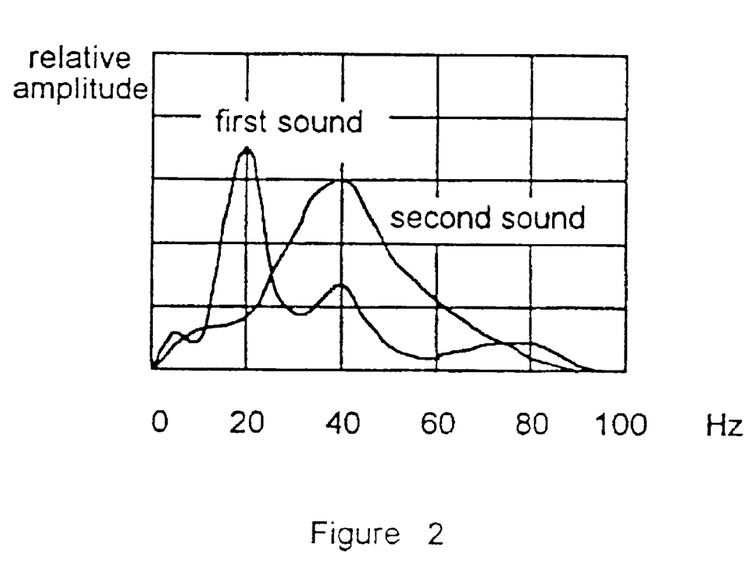
FIG. 2 shows frequency spectra of the first and second sound.

The frequency spectra of the first and second sound averaged for a long measuring time are shown in FIG. 2. However, there may be short time periods, when the frequency components differ substantially from the average distribution. In a typical case the low-frequency components disappear from the first sound. Because of the temporary variations of the spectrum, the curves of FIG. 2 are unusable for the reliable distinction of the two wounds.

The invention is based on the results of a large number of measurements showing that here is a significant difference between the power densities of the first and the second sound measured in a short time. This phenomenon can be well indicated on the spectral distribution of the power density determined for a relatively short time window. Analyses on large number of fetuses in the range of 25–80 Hz have shown, that there are some characteristic features of the power-time functions measure on frequencies of the upper and lower part of the range. Because the disturbing effect of the maternal heartbeat sounds, frequencies under 25 Hz are excluded from the analysis. Furthermore, components above 80 Hz were neglected, since the power density falls there very rapidly.

The following discussion is directed to a lower test frequency $f_a$ being between 25 and 35 Hz and relevant power density $P_a(t)$, and a higher test frequency $f_b$, being between 55 and 65 Hz, and relevant power density $P_b(t)$. Four typical signal curves of time functions of these components are shown in FIG. 3, where the $P_a(t)$ and $P_b(t)$ curves are computed for $f_a$=30 Hz and $f_b$=60 Hz and averaged for time windows $t_{wa}$=60 ms and $t_{wb}$=40 ms assigned to said two test frequencies. The length of these time windows should be longer than one and shorter than three periods of the test frequency.

In FIG. 3/a both curves have one peak at the first sound and one at the second sound. As observed, in most of such cases the peak of $P_b(t)$ precedes with 15–40 ms the peak of $P_a(t)$, so the criterion 15 ms<$t_{a1}-t_{b1}$<40 ms is fulfilled. In addition, for the value of $P_b(t)$ at $t=t_{a1}$ and the peak value of $P_b(t_{b1})$ the criterion $P_b(t_{a1})/P_b(t_{b1})$<0.3 is satisfied where $t_{b1}$ is the time of the first peak. On the other hand, at the second sound the two peaks are very near together, i.e. the criterion −15 ms<(Error, the marker is not true $t_{a2}-t_{b2}$)<15 ms is satisfied.

In FIG. 3/b $P_b(t)$ has two peaks at the first sound. However, the criterion of $P_b(t_{a1})/P_b(t_{b1})$ 0.3 is still satisfied. The second sound is similar to that in FIG. 3/a. In FIG. 3/c $P_a(t)$ has two, Pb(t) one peak at the first sound. In most of such cases for the time of the first peak $t_{a1}$ of the first peak $P_a(t)$ the criterion of −15 ms<($t_{a1}-t_{b1}$)<15 ms is satisfied. In FIG. 3/d both $P_a(t)$ and Pb(t) have two peaks at the first sound. In most of such cases this sound is a first one and no further criterion should be considered.

Figure 4:
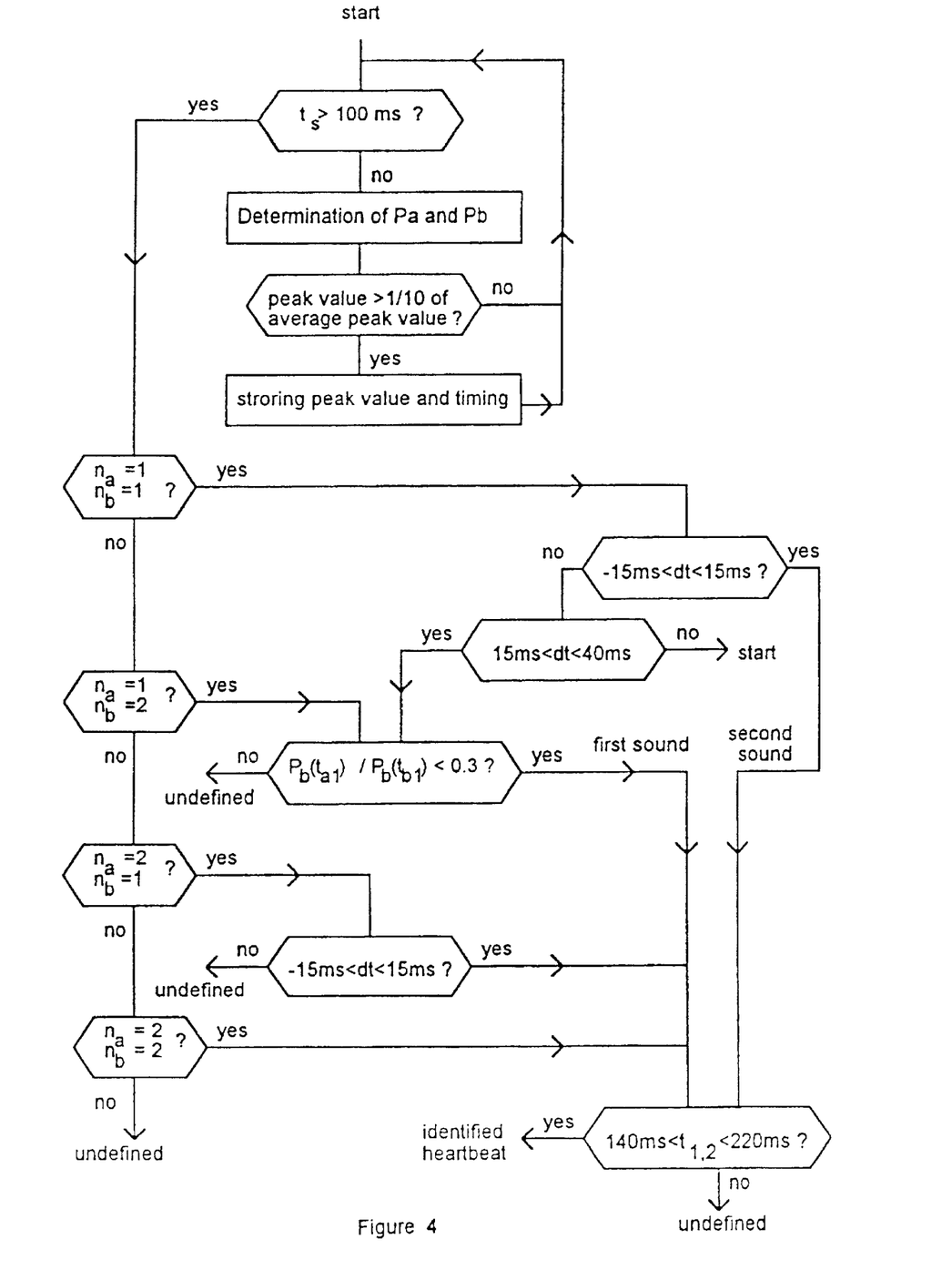
FIG. 4 is the flow-diagram of separation and identification of first and second sound of fetal heartbeat.

A large number of tests have proved that in most cases the overwhelming part of fetal acoustic heart signals is quite similar to one of these cases, meets the conditions mentioned above, consequently the first and the second sound can be reliably distinguished. A flow diagram of the distinction of the sounds is shown in FIG. 4, where dt denotes the time difference between the first peaks of $P_a(t)$ and $P_b(t)$, furthermore $t_{1,2}=t_{a2}-t_{a1}$ is the time difference between the first and second sounds and, finally, the number of peaks of $P_a(t)$ and $P_b(t)$ detected during the inspection time interval of 80 to 120 ms, preferably $t_s=100$ ms are denoted to $n_a$ and $n_b$, respectively.

As seen on the flow diagram, the method continuously searches for local peaks of $P_a(t)$ and $P_b(t)$, which should exceed the 1/10 part of the average of, e.g. five preceding peak values. Finding the first acceptable peak the counting of the inspection time $t_s$ begins. During this time all accepted local peaks are stored, counted and averaged. Ending the inspection time the number of peaks are examined and sounds are classified considering the number, values and timing of the peaks. Sounds can be classified as first sounds, second sounds or undefined sounds. This classification allows identification of fetal heart sounds with high reliability. The classification is executed on the basis of various criteria constituting a substantial aspect of the invented method and discussed in detail later.

In an identified first sound is followed by an identified second one within a subsequent closing time range between 140 and 220 ms, then the pair of sounds are identified as a heartbeat. The actual FHR value is calculated from the reciprocal of the repetition time of two subsequent identified heartbeats as $FHR=60/T_{rep}$, where $T_{rep}$ is the repetition; time. To improve identification reliability the duration of said closing time range can be continuously adjusted depending on the average of previously measured closing times.

A first or a second sound detected separately, i.e. without its corresponding pair can be utilized to substitute a not identifiable heartbeats. If the time difference of two identified heartbeats is approximately twice as long as the previously calculated ones, i.e. 1.4 to 2.6 multiple thereof, furthermore, a first or second sound was found without a matching pair between two heartbeats, then the half of the measured time difference can be considered for FHR calculation.

The theoretically exact estimation of power values needs numerous arithmetic operations that cannot be completed by a low-power electronic circuit within a sampling period. To overcome this problem significant simplifications are introduced in the computations and the word length is truncated, without sacrificing the distinction of the first and second sound. Since the power consumption of advanced CMOS circuits is proportional to the number of operations this number should be substantially reduced. This can be accomplished by utilizing an application-specific processor.

An arrangement of the apparatus implementing the invented method discussed above is shown in FIG. 5. Acoustic signals generated by a fetus are converted into low-level electric signals by a specially constructed sensor 1 placed to the surface of the maternal abdomen. Said sensor 1 is connected to an analog unit 2. An active filter 3 comprised in said analog unit 2 enhances signals in a frequency band from 25 to 80 Hz. Filtering out frequency components below 25 Hz and above 80 Hz separates signal components to be analyzed from the disturbances consisting of maternal heart sounds and external noises.

Figure 5:
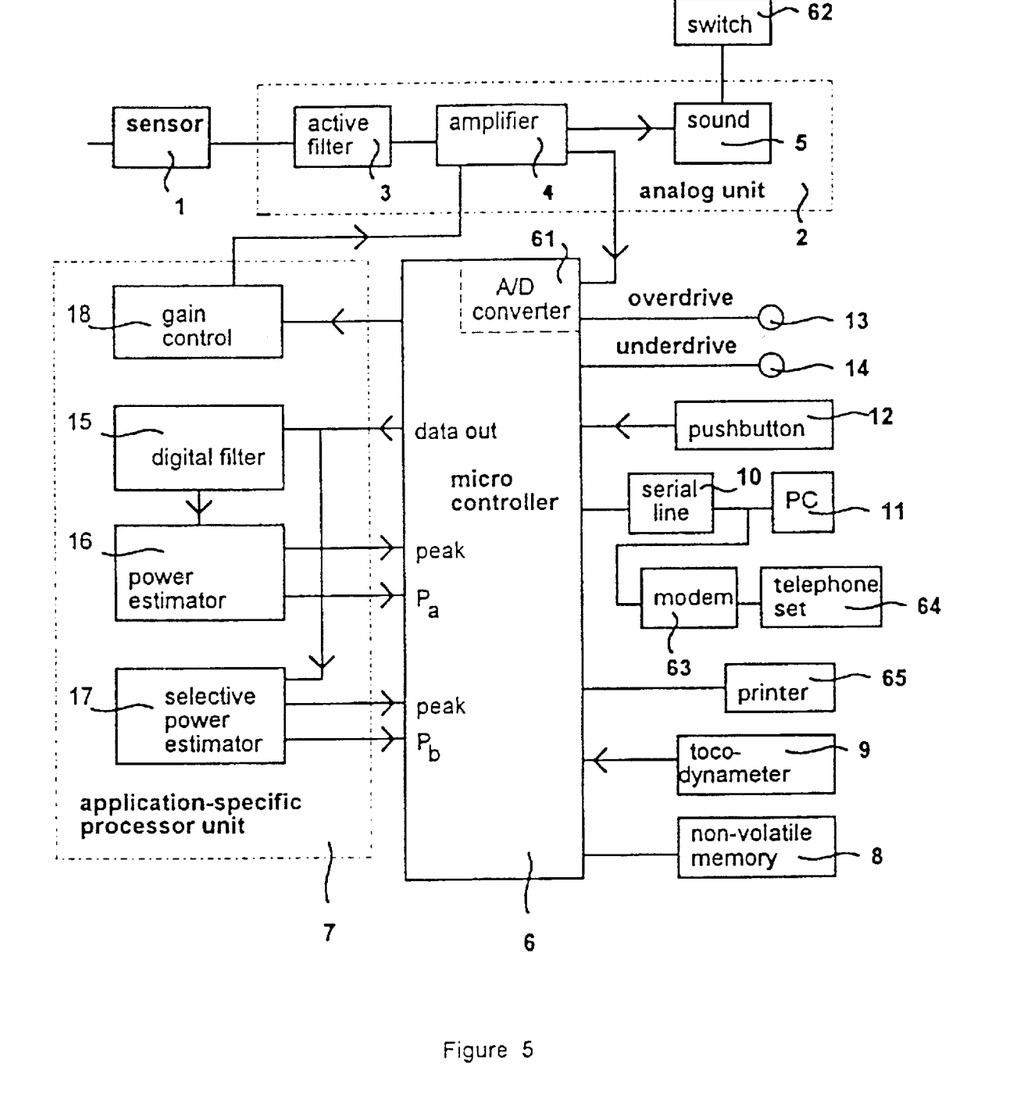
FIG. 5 shows block diagram of a preferred embodiment of the invented apparatus adapted for continuous registration of fetal heart rate.

Said analog unit 2 further comprises an amplifier 4 having adjusted gain, said amplifier 4 amplifies the output signal of filter 3 to a level required for subsequent analog to digital conversion. For this purpose continuous gain control compensates level variations of the received signal. Said analog unit 4 comprises a sound unit 5 connected to an output of said amplifier 4 and containing a power amplifier, a frequency transponder and a loudspeaker to make the input signal audible. The frequency shift by, e.g., 150 Hz avoids instability of the power amplifier and makes sound more perceptible. This transponded audible sound of heartbeat makes easier to find the optimal location of sensor 1 on the maternal abdomen. Preferably a switch is provided for to switch off this sound.

The output of amplifier 4 is fed to an analog to digital converter 61 comprised in an advanced, low-power microcontroller 6. Said converter 61 converts amplified signals with a sampling time of T=2 to 4 ms and forwards digitized data to an application specific processor 7 for estimating powers $P_a(t)$ and $P_b(t)$ and detecting their local peaks. Accordingly, said application specific processor 7 includes a gain control unit 18, a digital filter 15, a first selective power estimation unit 16 connected to said digital filter 15 and a second selective power estimator unit 17.

Said first selective power estimator unit 16 has a first output providing the actual value of $P_a(t)$ and a second output providing a signal if a local maximum or peak of $P_a(t)$ is detected. More detailed descriptions of digital filter 15 and first selective power estimator unit 16 are given later referring to FIG. 7 and FIG. 8, respectively.

Processor 7 further includes a second selective power estimation unit 17 having a first output providing the actual value of $P_b(t)$ and a second output indicating peaks of $P_b(t)$.

Microcontroller 6 performs arithmetic operations of the preferred algorithm demonstrated by the flow diagram of FIG. 4. Microcontroller 6 includes a number of circuitry well-known in the art and not mentioned separately and allowing the microcontroller 6 to perform all functions of an also separately realizable identification unit for identifying or qualifying sound bursts. Said qualification is based upon time, value and sequence of local peak of $P_a(t)$ and $P_b(t)$, respectively, and preformed as disclosed herein and demonstrated by FIG. 4.

Receiving a signal indicative of a peak said microcontroller 6 reads out the actual values of $P_a(t)$ and $P_b(t)$, and evaluates these values. As a result of this process received sound bursts are qualified as a first or a second or unidentified sounds, furthermore, a heartbeat will be identified, when a corresponding pair of a first and a subsequent second sound is found. The reciprocal of the repetition time of identified heartbeats provides an actual FHR value, which is continuously stored in a non-volatile memory 8 connected to and controlled by said microcontroller 6. Stored data can be read out, e.g. by a personal computer through the microcontroller 6 using a standard serial line 10. The high-capacity non-volatile memory 8 is capable to store the data of a measurement more than one week long, and makes thereby the apparatus suitable for long-term home monitoring. The personal computer may be omitted by connecting a line printer directly to serial line 10 forming in this way a cost-effective configuration for FHR printout.

A critical point of the invention is the accuracy of the digitized input. To achieve sufficient accuracy, full range of an 8-bit A/D conversion should be exploited. To assure this, a gain control unit 18 is included in processor 7 and is connected to microcontroller 6 and to the gain control input of amplifier 4. The average value of detected peaks should be set equal approximately to the 75% of the full scale. The gain control unit 18 is regulated by said microcontroller 6, which continuously calculates average values of the detected peaks of $P_a(t)$ and $P_b(t)$.

As a consequence of this adjustment the amplifier 4 or even the analog to digital converter 61 will be sometimes overdriven by very high disturbances. However, these highly disturbed time periods can be left out of consideration because they do not provide information. It is important however, that after them the system should recover to its normal operation as fast as possible.

The gain control unit 18 comprises a digital to analog converter, or can be realized as a manually adjustable resistor. Since the operation is not sensitive to gain accuracy, the resolution of digital-analog converter in gain control unit 18 can be less than 5 bit.

Preferably the apparatus comprises some conventional units such as a tocodynameter 9, an input device 12 in form of one or more pushbuttons, optionally light emitting diodes 13 and 14, all in connection with said microcontroller 6. It controls the tocodynameter 9, which monitors continuously maternal womb contractions. Said input device 12 allows the mother to indicate the subjective feeling of the fetal movement. The optional light emitting diode 13 indicates overdrive of the amplifier 4 due to extremely large input acoustic signal, light emitting diode 14 signalizes underdrive, when extremely low input level makes heartbeat identification problematic. The serial line 10 realizes a standard link between the microcontroller 6 and an external personal computer.

Figure 6:
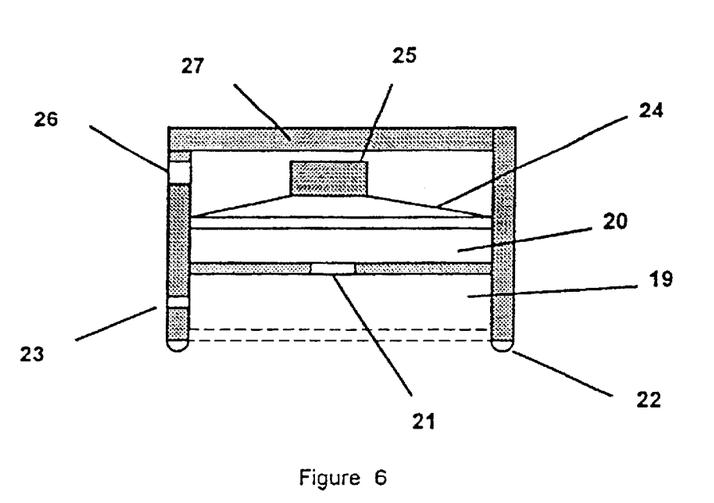
FIG. 6 is a cross-sectional view of preferred embodiment of the invented sensor for use with the apparatus of FIG. 5.

The structure of sensor 1 is shown in FIG. 6. This design provides maximum sensitivity in the frequency band to be analyzed. Sensor 1 comprises a hollow body 27 divided into a first, a second and a third chamber 19, 20 and 25, respectively. First chamber 19 is open at one side and is coupled to second chamber 20 via an opening 2 formed in the partition wall between said first chamber 19 and second chamber 20. The construction of the external first chamber 19, the internal second chamber 20, and the coupling between them serve to obtain advantageous frequency characteristics. The lower side of the first chamber 19 is confined by the skin of the maternal abdomen, whereas the sidewall is rigid. The first chamber 19 is acoustically closed by elastic ring 22 provided at the periphery of first chamber 19. The surrounded part of the skin surface acts as a membrane. The volume of first chamber 19 is 250 to 350 cm$^3$. Ring 22 has an external diameter of 70 to 80 mm, its width is 5 to 6 mm and the pressure by which the sensor is touching the skin is 0.002 to 0.003 kp/cm$^2$. This pressure is accomplished by a flexible belt.

The upper wall of second chamber 20 is formed by a sensitive membrane of an electroacoustic converter 24, whereas its sidewall is rigid. The volume of second chamber 20 is 130 to 200 cm$^3$. This central boring 21 between first chamber 19 and second chamber 20 realizes acoustic coupling of the chambers. The diameter of the boring 21 is 2.5 to 3 mm. The volume of first chamber 19 and second chamber 20, furthermore the size of central boring 21 accomplish acoustic matching between the abdomen and the electroacoustic converter 24.

The electroacoustic converter 24 is a highly sensitive dynamic converter with elastic membrane, however, other types with sufficient sensitivity, e.g. piezoelectric converters, can also be used. To avoid overdrive of the active filter 3 by low-frequency components of the maternal heart sound, it is suitable to terminate the electroacoustic converter 24 with high impedance, cutting off thereby low frequency components.

On the sidewall of first chamber 19 a first boring 23 of diameter 0.5 to 3 mm preferably 0.8 mm is formed to avoid damping effect of the air mass transferring the vibration of the skin. Said first boring 23 forms a high-pass filter acting as damping for the maternal heart sounds. Said third chamber 25 is located on the opposite side of the membrane of said electroacoustic converter 24 and is communicating with the atmosphere through a second boring 26 of diameter 0.5 to 3 mm preferably 0.8 mm formed in the sidewall of hollow body 27. Said second boring 26 between the third chamber 25 and the free air reduces the effect of the airbag developed behind the electroacoustic converter 24, and provides protection against background noise by compensation.

Figure 7:
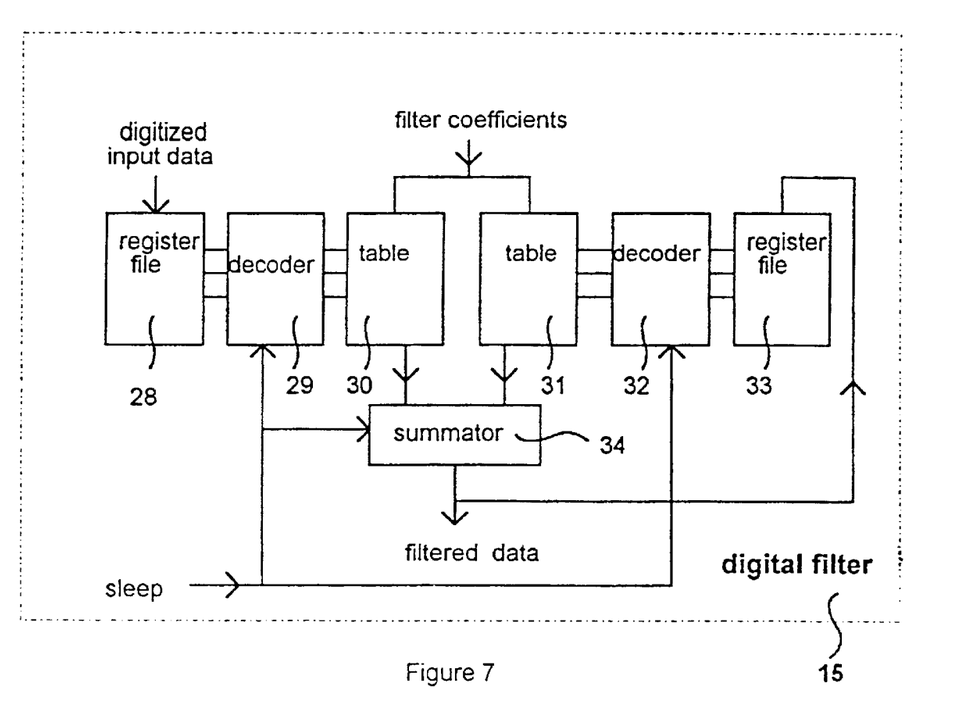
FIG. 7 is a detailed block diagram of a preferred embodiment of the digital filter circuit of FIG. 5.

To estimate the powers $P_a(t)$ and $P_b(t)$ the frequency components of $f_a$ and $f_b$ should be selected from the 25–80 Hz passband. The application of active filters is unsuitable for this purpose because of the large number of discrete components required for the high selectivity. More advanced are the recursive digital filters, the $y_n$ output of which is given by the relationship $$y_n = \sum_{k=0}^{M} a_k d_{n-k} + \sum_{k=1}^{N} b_k y_{n-k},$$

where n is the number of sampling, d(n−k) is the (N−k)th previously sampled input data, y(n−k) is the (n−k)th previous filtered data, $a_k$ and $b_k$ are the filter coefficients, and M and N represents the orders of the filter. As seen from the relationship, every sampling requires M+N+1 number of multiplication, which results to high power consumption of the arithmetic unit. The power consumption is reduced by the digital filter 15 shown in FIG. 7.

This exemplary digital filter 15 comprises a register file 28 having a serial-in, parallel-out structure. The m-bit long digitized input data are loaded in the register file 28, which store (M+1) number of words and parallel output of each register provide an m-bit word. Preferred value of m is 8. Upper register of register file 28 holds actual data, the lower stores the oldest one. These outputs are connected to inputs of a segmented first decoder 29 comprising the same (M+1) number of m to $2^m$ decoders or segments as the number of registers in register file 28. Each segment has $2^m$ number of outputs which are connected to a designating line in a corresponding segment of a memory containing data words of the look-up first look-up table 30. Each designating line designates a corresponding word in the corresponding segment of first look-up table 30. Consequently, (M+1) number of data words are designated at the same time. The words of the segments, corresponding to the first member of the above formula contain the product of the input data and the filter coefficients $a_k$ ($a_0$ to $a_6$). The word length of first look-up table 20 is truncated to 16 bit, whereby the size is $2^m$(M+1) words, i.e. 7×256=1792 words of 16 bit comprised in (M+1)=7 segments. The first look-up table 30 includes an internal bus comprising a corresponding number of, i.e. 16 lines. Each segment of first look-up table 30 has an activating input allowing to transfer designated words one-by-one to this bus. The bus, i.e. the output of first look-up table 30 is connected to the firs summator 34. The designated words of the segments are read out sequentially and summed by the said first summator 34. The sum is truncated to m bit. Coming new data to the filter, the contents of the register file 28 is shifted down. As a result, the data will now designate the next segment of the first look-up table 30.

Digital filter 15 comprises a further second register file 33, a further second decoder 32 and a further look-up second look-up table 31 having the same structures and interconnections as outlined above. The only distinction is that input data are received from the output of said first summator 34 and the number of segments is N.

Applying recursive type digital filter the preceding values of filtered data are also used. The values are fed back to the second register file 33, organized as a serial-in, parallel-out storing unit and containing N words by m-bits. The operation of second register file 33, second decoder 32 and look-up second look-up table 31 is similar to that of register file 28, first decoder 29 and first look-up table 30. The size of the second look-up table 31 is $2^m$ N=1536 words by 16 bit comprised in N=6 segments. The designated words of the segments of first look-up table 30 are read out sequentially and summed by the said first summator 34. The sum is truncated to m-bit. After summation of the M+N+1 products the first summator 34 outputs filtered data. Thus the upper register of second register file 33 contains the last filtered data.

A further advantage of digital filtering compared to analog technique is that a sleep mode can be introduced between the heartbeats to suspend filtering for a given time, thus decreasing the power consumption of the circuit. Receiving a sleep signal corresponding circuits turn into powder down mode and output data of the filter fall to zero. The sleep signal is generated by the microcontroller 6 after identification of a heartbeat. This sleep mode is 80 to 140 ms, preferably 120 ms long counted from the respective second sound, i.e. $t_{a2}$. During this sleep period no heartbeat is expected.

Using look-up tables with preloaded products of multiplication reduces highly the power consumption of the circuit. The tables may be EPROM memories with burned-in values, providing the lowest power requirement and the fastest operation. However, in this case the filter characteristics cannot be modified. To allow modification of the characteristics, the table should be stored in read-write memories. The memory will be loaded by the microcontroller 6 depending on the evaluation of the power functions. This allows modifying filter characteristics while carrying out measurement depending on the spectrum of acoustic signals received from the fetus. Modification can be effected by experienced personnel or an appropriate software can be provided for. In addition, the filter coefficients can be calculated by a personal computer considering the progress of gestation and the estimated weight of the fetus in advance. These values can be loaded in the microcontroller 6 as starting data.

The estimation of the power $P_b(t)$ measured at the frequency $f_b$ and, the detection of its peak values is carried out by the application-specific processor 7. For signals with zero mean the power of $n_w$ sampled data can be estimated by the relationship $$P = \sum_{i=0}^{n_w-1} d_i^2,$$

where $d_i$ is the ith sampled data and P is the summed power for the number $n_w$ sampling. As seen, to calculate the power in every sampling cycle it is needed to store and sum the square of number $n_w$ data in every cycle, corresponding to the length of the mowing window. The large number of data to be stored increases unsuitably the required memory capacity, furthermore, the large number of arithmetic operations enhances the power consumption.

Since the sampling frequency 1/T is much higher, than the highest component in the frequency band to be analyzed, some basic reductions may be introduced in the relationship above. The time function of the power will be averaged for j cycles, furthermore, the preceding value will be utilized for calculation of the actual power value corresponding the relation $$P_n = P_{n-j} + \sum_{i=n-j}^{n} d_i^2 - \sum_{i=n-n_w-j}^{n-n_w} d_i^2 = P_{n-j} + P_{in} - P_{out},$$

where $P_n$ is the calculated power in the nth cycle, $P_{n-j}$ is the power calculated before j cycles and $n_w$ is the size of the window expressed in sample numbers, which should be a multiple of j. In addition, $P_{in}$ is the power entering as the window moves forward and $P_{out}$ is the power to be subtract. Using this simplified relationship the number of summation of the squared samples are reduced by j, furthermore, the number of sums to be stored is only $n_w/j$.

Figure 8:
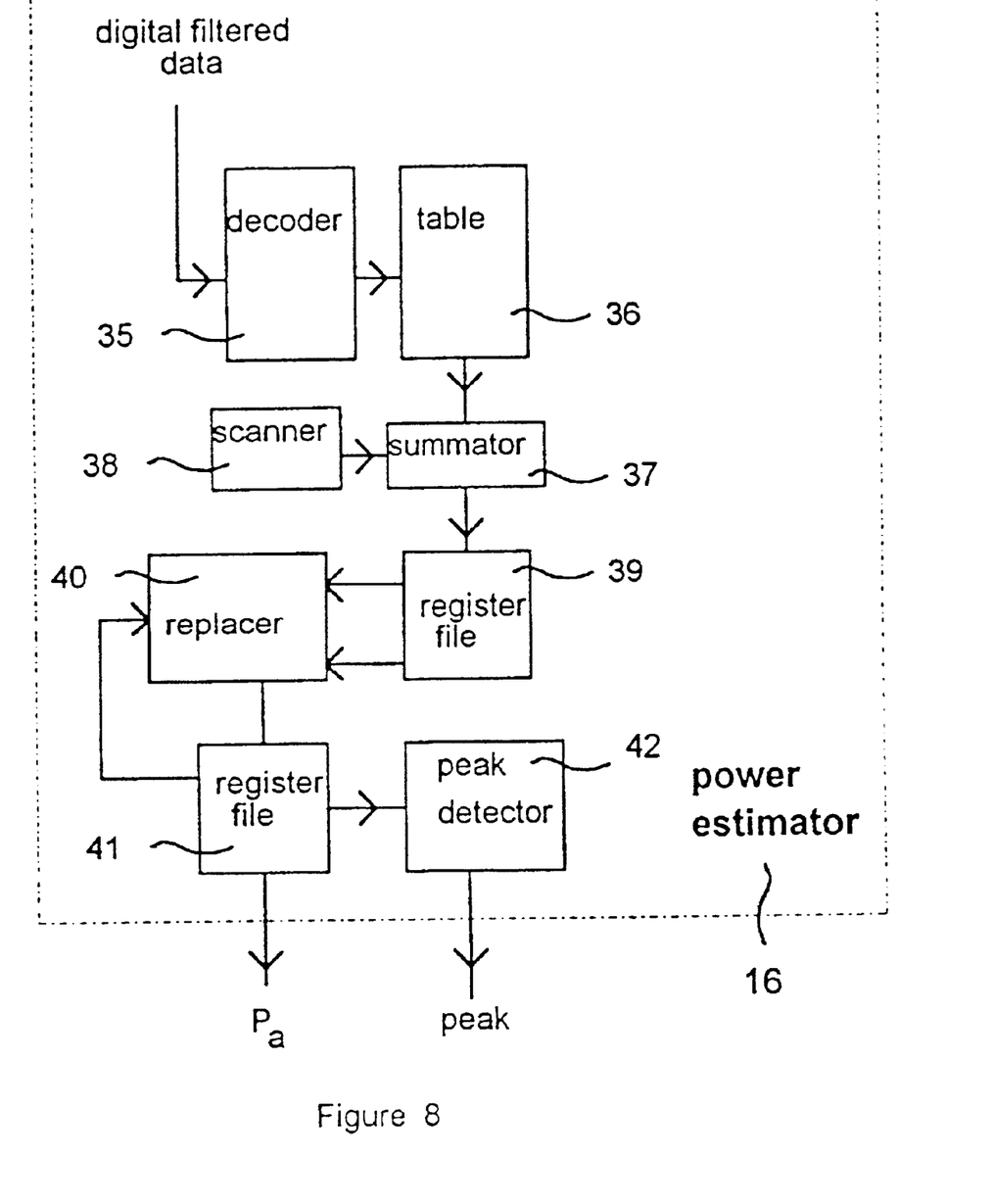
FIG. 8 is a detailed block diagram of a preferred embodiment of the power estimation circuit of FIG. 5.

The number of computation can be further reduced, if the squaring is accomplished by the utilization of a preloaded table. The schematic of the first selective power estimator unit 16 as one solution of the computation is shown in FIG. 8.

The first selective power estimator unit 16 can be advantageously designed to include an m to $2^m$ third decoder 35 the outputs of which are connected to the third look-up table 36. Output of the third look-up table 36 is connected to a summator interconnected with a scanner 38.

The digitally filtered m-bit data control the m to $2^m$ third decoder 35, which decodes an address. The address designates a word of the third look-up table 36, which holds the square value of the address truncated to 16 bit. The size of the third look-up table 36 is $2^m$ words by 16 bit. The second summator 37 reads out and sum j-times consecutively the designated words, corresponding to the $P_{in}$ member of the relationship. The j consecutive steps are controlled by the scanner 38. The power value $P_{in}$ is loaded into the third register file 39, in which the data are shifted down in every j step. The upper register of third register file 39 holds now the new data $P_{in}$ and the lowest register contains the leaving data $P_{out}$. Both registers are parallel connected to the replacer 40, which substitutes $P_{out}$ by $P_{in}$ subtracting it from the previous value $P_{n-j}$ and adding to them the new one, corresponding to the relationship. The previous value $P_{n-j}$ is read out from the upper register of fourth register file 41. The calculated new value $P_n$ is loaded into the upper register of the fourth register file 41, in which the data are shifted down in every j step. The data are readable by the microcontroller 6. The fourth register file 41 contains five 16 bits words which are connected parallel to the first peak detector 42.

Figure 9:
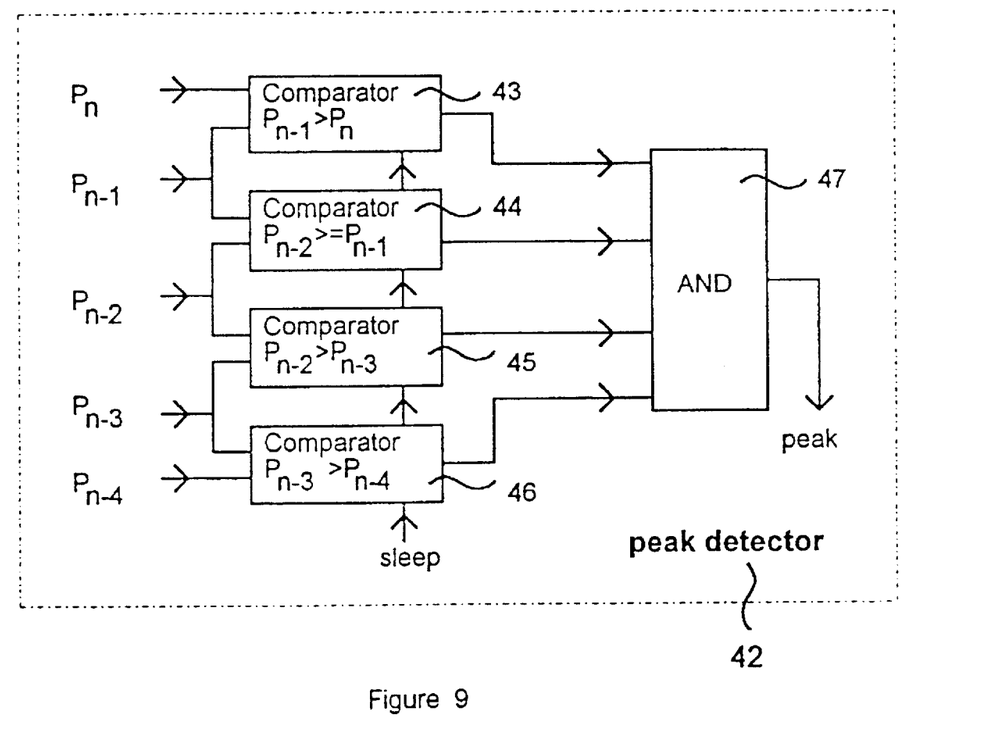
FIG. 9 is a detailed block diagram of a preferred embodiment of the selective power estimation circuit according to FIG. 5.

The first peak detector 42 serves for the announcement of the maximum value of the power $P_a(t)$. The circuit schematic is shown in FIG. 9. The adjacent pairs of the sequentially following $P_n$, $P_{n-1}$, $P_{n-2}$, $P_{n-3}$, and $P_{n-4}$ values are compared by the comparators 43, 44, 45, and 46, respectively. Comparison criteria are as follows: $P_n<P_{n-1}$; $P_{n-1}$ $P_{n-2}$; $P_{n-2}>P_{n-3}$; $P_{n-3}>P_{n-4}$. As it follows from the above criteria comparator 44 provides also logic high state when the amplitudes are equal in order to take into account the case when two equal maximum values are detected. When all conditions are satisfied, the value $P_{n-2}$ represents the peak of the power function and the AND gate 47 transmits a signal to the microcontroller 6. The microcontroller 6 checks the amplitude of the peak and rejects them, if the amplitude is smaller than the $\frac{1}{10}$ part of the average amplitude of the previously registered peaks.

To keep power consumption low the microcontroller 6 turns over first peak detector 42 in sleep mode, whenever a heartbeat is identified and so no beat is expected for the coming 120 ms time interval.

The power $P_b(t)$ of the frequency component $f_b$ is estimated also by the application-specific processor 7 using the moving-window periodogram method by the relationship $$S_v = \sum_{i=0}^{n_{wb}} V_i; \quad V_i = d_i * \sin(2\pi f_b i / n_{wb}) * Ba(i);$$

$$S_w = \sum_{i=0}^{n_{wb}} W_i; \quad W_i = d_i * \cos(2\pi f_b i / n_{wb}) * Ba(i);$$

where $d_i$ is the ith data sampled and digitized from the unfiltered signal, $n_{wb}$ is the size of window in number of sample times, $Ba(i)$ stands for the triangular correction function of the Bartlett window, and $P_b=(S_v^2+S_w^2)/n_{wb}$ is the power in the actual time window for the frequency $f_b$.

Figure 10:
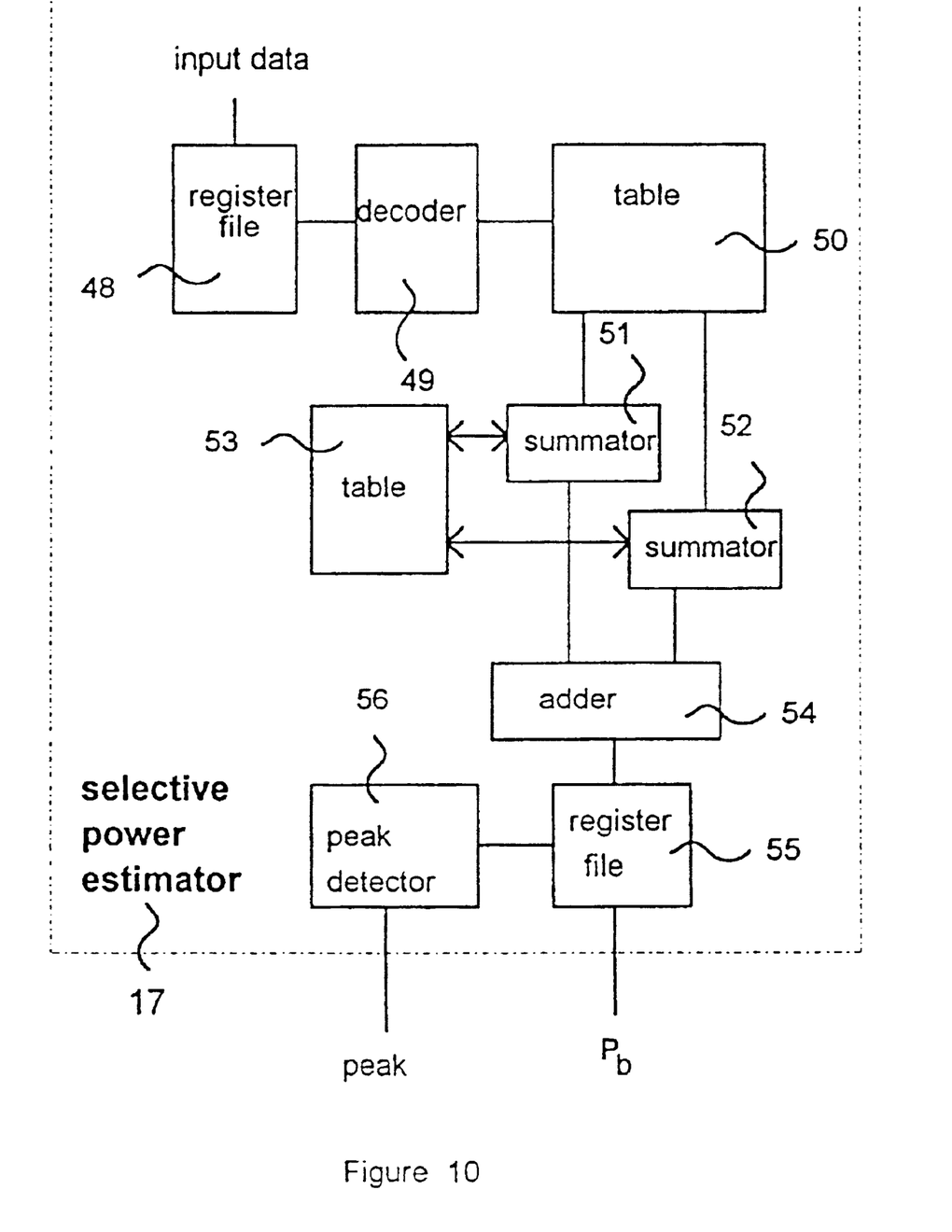
FIG. 10 is a detailed block diagram of a preferred embodiment of the peak detector circuit of FIGS. 8 and 9 for the indication of peak values $P_a(t)$ and $P_b(t)$.

The schematic diagram of the second selective power estimator 17 for carrying out the above computations is shown in FIG. 10. This preferred embodiment of the second selective power estimator unit 17 comprises a fifth register file 48 having a serial-in, parallel-out structure. Fifth register file 48 stores the last $n_{wb}$ number of data and shifts them down in each step. The digitized, m-bit input data $d_i$ containing all frequency components between 25–80 Hz are loaded in the fifth register file 48. The upper register holds actual data, the lower stores the oldest one. Each register has a parallel output connected to a segmented m to $2^m$ fourth decoder 49. Each parallel output of fifth register 48 controls one segment of an m to $2^m$ fourth decoder 49. Each segment decodes its input data and designates two corresponding words stored in a segmented fourth look-up table 50, which stores $V_i$ and $W_i$ products of the above formula, truncated to 16-bit. Said fourth look-up table 50 can comprise two tables similar to look-up tables 30 and 31 of digital filter 15. Consequently, the size of the fourth look-up table 50 is $2^m*n_{wb}$ words, divided into $n_{wb}$ segments. The fourth look-up table 50 is connected to the third and fourth summators 51, 52. The designated products of $V_i$ are summed by said third summator 51, whereas the designated product of $W_i$ by said fourth summator 52. The summation is carried out $n_{wb}$ times consecutively for all segments, corresponding to the above formulae. Summators 51 and 52 are interconnected with fifth look-up table 53 comprising squared values of input data. On the basis of summed products, said third summator 51 as well as said fourth summator 52 read out relevant squared values from fifth look-up table 53 and transfers the squared values to an adder 54 connected to the output of third and fourth summators 51, 52.

The squared values transferred by said third summator 51 and said fourth summator 52 are added by adder 54 according to the above formula. This value will be loaded in a sixth register file 55 connected to the output of said adder 54. Said sixth register file 55 has a serial-in, parallel-out structure and stores the last five values of the power $P_b$. Parallel outputs are connected to a second peak detector 56, which has the same structure as first peak detector 42 discussed above. Comparing amplitudes of the last five power values an incoming peak can be detected and indicated to the microcontroller 6.

The size of fourth look-up table 50 can be reduced by rounding the product values. In this case, the least significant bits are cut down truncating hereby the word length to $m^*<m$. Preferred value of $m^*$ is 6 or 7. As a result, there are more $d_i$ input data assigned to the same products, which can be drawn together in a common table segment containing $2^{m^*}$ words. This common segment can be addressed by OR combining outputs of related decoder segments. In this way the size of table can be significantly reduced without sacrificing accuracy of $P_b(t)$.

After identification of each heartbeat the microcontroller 6 turns over the second selective power estimator unit 17 into sleep mode for 120 ms time interval to keep average power consumption low.

The reliability of heartbeat identification can be increased by the application of a second sensor placed to a location where the detection of the maternal heartbeat sounds is maximal. To identify maternal heartbeats is very easy because of its large amplitudes. Utilizing these identified signals to inhibit fetal sound measurement temporary, the disturbing effect of the maternal sounds can be reduced.

The program running on the person computer reads out the FHR and tocodynameter data from the non-volatile memory 8. Furthermore, it reads out data relating to the patient and the time of measurement. A user-friendly paging software serves for the survey of large data blocks.

For telemetric home care applications the equipment can be completed with a modem to send data into the hospital or to the doctor's private personal computer. The equipment can be provided with a handler routine for direct driving of a printer thus eliminating the need for a personal computer, when a common printout is required only.

The application specific processor 7 is implemented in a low-power CMOS circuit. In order to minimize power consumption it is designed for minimum internal parasitic capacity to be charged during one cycle of sampling. If higher battery current is allowed, then some operations performed by the application specific processor 7 can be carried out by the microcontroller 6 instead. The evaluation of the detected peaks by the microcontroller 6 takes only some percentage of time thus relevant power consumption is negligible.

What is claimed is:

1. A method for measurement of fetal heart rate on the basis of acoustic signals originating from heat activity of a fetus and detectable on a maternal abdomen, the method comprising the steps of:

measuring acoustic signals of fluctuating intensity originating from the heart activity of the fetus;

converting said acoustic signals into electric signals;

determining power levels ($P_a$, $P_b$) of said signals at a lower and at a higher test frequency ($f_a$,$f_b$), said lower and higher frequencies ($f_a$,$f_b$) being, respectively, in a lower and a higher frequency band of a frequency range of 20 to 80 Hz;

detecting and storing local peak values ($P_{a1}$, $P_{a2}$; $P_{b1}$, $P_{b2}$) of said power levels ($P_a$, $P_b$) at different times ($t_{a1}$, $t_{a2}$; $t_{b1}$, $t_{b2}$) during an inspection period ($t_s$) following the first one of said detected local peaks;

counting numbers ($n_a$, $n_b$) of said peaks of power levels during said inspection period $t_s$;

determining time differences between the times of detection of said peak values ($P_{a1}$, $P_{b1}$, $P_{a2}$, $P_{b2}$) within said inspection period ($t_s$);

identifying the detected peak as a said second sound, provided that said number ($n_a$) of local peaks of said power level ($P_a$) is one and said number ($n_b$) of local peaks of said power level ($P_b$) is one and said time difference (dt) between said peak values ($P_{a2}$, $P_{b2}$), is smaller than 15 ms;

identifying the detected peak as a said first sound, provided that said number ($n_a$) is one and for said time difference (dt) the criterion 15 ms<dt<40 ms is satisfied and for said power level ($P_b$) measured at said time ($t_{a1}$)

corresponding of said peak values ($P_{a1}$) of said power level ($P_a$) the criterion ($P_b(t_{a1})$)/$P_{b1}$<0.3 is satisfied;

identifying the detected peak as a said first sound provided that said number ($n_a$) is one and said number ($n_b$) is two and for said power level ($P_b$) measured at the time ($t_{a1}$) of said peak values ($P_{a1}$) of said power level ($P_a$) the criterion ($P_b(t_{a1})$)/$P_{b1}$<0.3 is satisfied;

identifying the detected peak as a said first sound, provided that said number ($n_a$) is two and said number ($n_b$) is two;

classifying a pair of identified peaks as heartbeat, provided that the measured time difference ($t_{1,2}$) between the said first and second sound is in the range of 140 ms to 220 ms; and calculating the fetal heart rate from the time difference between two consecutively identified heartbeats.

2. The method as claimed in claim 1 wherein said determination of power level ($P_a$) at said lower test frequency ($f_a$) includes averaging said power level ($P_a$) for a time window of 30 to 90 ms; and said determination of power level ($P_b$) at said higher test frequency ($f_b$) includes averaging said power level ($P_b$) for a time window of 20 to 60 ms.

3. The method as claimed in claim 1 or 2, wherein local peak values ($P_{a1}$, $P_{a2}$; $P_{b1}$, $P_{b2}$) of power levels ($P_a$, $P_b$) are detected if their values exceed the 1/10 part of the average of previously detected peak values.

4. The method as claimed in claim 1, wherein said lower testing frequency band ranges from 25 to 35 Hz and said upper testing frequency band ranges from 55 to 65 Hz.

5. The method as claimed in claim 1 wherein said testing frequencies ($f_a$, $f_b$) are predetermined according to the time of gestation and estimated weight of fetus, and said predetermined test frequencies are applied as starting values at the beginning of the measurement.

6. The method as claimed in claim 1 wherein the values of said testing frequencies ($f_a$, $f_b$) are continuously adjusted to obtain maximum values for said local peaks of said signal power.

7. The method as claimed in claim 1 wherein said inspection time ($t_s$) is longer than 80 ms and shorter than 120 ms.

8. The method as claimed in claim 1 wherein said inspection time ($t_s$) is shortened if identification of said first sound or said second sound is completed.

9. The method as claimed claim 1 wherein the time difference ($t_{1,2}$) between the first and second sound is longer than 140 ms and shorter than 220 ms. and said time difference ($t_{1,2}$) is continuously adjusted on a previously calculated average of the time difference ($t_{1,2}$).

10. An apparatus for measuring fetal heart rate, the apparatus comprising:

an acoustic sensor (1) for sensing acoustic vibrations derived from a fetus, said sensor adapted to be placed on a maternal abdomen;

an analog unit (2) for amplifying and enhancing frequencies characteristic to fetal heart activity, the analog unit (2) including an amplifier (4) having adjustable gain for adjusting a signal level to be in a conversion range of an analog to digital converter (61) connected to the amplifier (4) which converts analog signals to digital sample values;

a first frequency selective power estimation unit (15, 16) for determining signal level at a lower test frequency ($f_a$) within a frequency range from 25 to 35 Hz;

a second frequency selective power estimation unit (17) for determining the signal level at a higher test frequency ($f_b$) with a frequency range from 55 to 65 Hz;

a first and second peak detector (42, 56) for monitoring said signal levels fluctuating in time and estimated by said first and second power estimation units (15, 16, 17) and establishing occurrence of local peaks of said signal levels;

an identification unit for identifying first and second heart sounds based upon the time and the sequence of said local peaks and for computing fetal heart rate according to the method of claim 1;

a storage means (8) for storing measured fetal heart rate values; and a communication port (10) for making said stored fetal heart rate values accessible for further evaluation.

11. The apparatus as claimed in claim 10, wherein said peak detectors (42, 56) include comparators (43, 44, 45, 46) connected to parallel outputs of said fourth and sixth register files (41, 55); and an AND gate (47) connected to outputs of said comparators (43, 44, 45 and 46) indicating the local peak of said power level ($P_a$, $P_b$).

12. The apparatus as claimed in claim 10, wherein said sound unit (5) includes a switch (62) adapted to turn on and off transponded and audible heart sounds.

13. The apparatus as claimed in claim 10, wherein said serial communication port (10) is adapted to be connected to a line printer.

14. The apparatus as claimed in claim 10, wherein the acoustic sensor (1) includes a hollow body (27) and an electroacoustic converter (24), located inside said hollow body (27) and having a sensitive membrane;

wherein said hollow body (27) is partitioned into a first, a second, and a third chamber (19, 20, 25);

said first chamber (19) being open at one side, and coupled to said second chamber (20) via an opening (21) formed in the partition wall between said first and second chambers (19 and 20), and having a first boring (23) on its sidewall communicating with the atmosphere;

said second chamber (20) having an upper partition wall formed by a sensitive membrane of an electroacoustic converter (24); and said third chamber (19) communicating with the atmosphere through a second boring (26) formed in the sidewall of the hollow body (27).

15. The apparatus as claimed in claim 14, wherein said electroacoustic converter (24) is an electrodynamic microphone having an elastic membrane.

16. The apparatus as claimed in claim 15, wherein an elastic ring (22) is provided at the periphery of said open side of said first chamber (19).

17. The apparatus as claimed in claim 10, further comprising a tocodynameter (9) for continuous measurement of maternal womb contractions.

18. The apparatus as claimed in claim 10, wherein said analog unit (2) includes an active filter (3) connected to said sensor (1), said amplifier (4) being connected to said active filter (3) and a sound unit (5) which is connected to said amplifier (4), the apparatus thereby amplifying, filtering and frequency transponding the input signal.

19. The apparatus as claimed in claim 10, wherein said analog to digital converter (61) is included in a microcontroller, said microcontroller (6) being adapted to evaluate data and control peripheral units.

20. The apparatus as claimed in claim 19, further comparing a standardized modem adapted to effect data transfer for telemetric measurements and for communicating with the microcontroller (6).

21. The apparatus as claimed in claim 19, wherein at least one of said first frequency selective power estimation unit (15, 16), said second frequency selective power estimation unit 17, said first peak detector (42) and said second peak detector (56) is included in the microcontroller (6).

22. The apparatus as claimed in claim 19, wherein at least one of said first frequency selective power estimation unit (15, 16), said second frequency selective power estimation unit (17), said first peak detector (42), said second peak detector (56) is included in an application-specific processor (7) connected to the microcontroller (6), said application specific processor (7) further comprising a gain control circuit (18) connected to the gain control input of said amplifier (4).

23. The apparatus as claimed in claim 17, wherein said storage means (8) includes a non-volatile memory (8) connected to said microcontroller (6) for storing measured fetal heart rate data and addition data provided by said tocodynameter (9).

24. The apparatus as claimed claim 19, wherein said communication port (10) is a serial communication port connected to the microcontroller (6) for connecting said apparatus to an additional computer via a standard serial communication line.

25. The apparatus as claimed in claim 19, further comprising an input device (12) connected to the microcontroller (6) for indicating subjective feeling of fetal movement.

26. The apparatus as claimed in claim 19, further comprising a light emitting diode (13, 14) connected to the microcontroller (6) for indicating amplifier overdrive and extremely low input signal level.

27. The apparatus as claimed in claim 26, wherein at least one of said frequency selective power estimation units (15, 16; 17) includes a digital filter (15) adapted to select frequencies within said frequency range and said power estimation unit is connected to the output of said digital filter (15).

28. The apparatus as claimed in claim 27, wherein said digital filter (15) includes:
   a register file (28) having serial-in, parallel-out structure and containing actual input data and preceding data to be considered on the course of digital filtering;
   a segmented decoder (29) consisting of decoder segments for separately decoding parallel outputs of said register file (28);
   a segmented look-up table (30) storing words to be designated separately by said segmented decoder (29) consisting of products ($a_k d_{n-k}$) where n is the number of sampling, $d_{n-k}$, is the (n–k)th previously sampled input data, $a_k$ are filter coefficients with k being in the range of k=0 to M, where M represents the order of the filter;
   a second register file (33) having serial-in, parallel-out structure and containing preceding filtered data used for actual filtering;
   a second segmented decoder (32) consisting of decoder segments for separately decoding parallel outputs of said second register file (33);
   a second segmented look-up table (31) storing words to be designated separately by said segmented decoder (32) consisting of products ($b_k y_{n-k}$), where $y_{n-k}$ are (n–k)th previous filtered data, $b_k$ are filter coefficients with k being in the range of k=1 to N, where N corresponds to the order of the filter;
   a summator (24) for consecutively reading out and summing each designed word of said table segments according to the following formula:

$$y_n = \sum_{k=0}^{M} a_k d_{n-k} + \sum_{k=1}^{N} b_k y_{n-k},$$

wherein $y_n$ is the actual filtered data, and the meaning of other designations are the same as above.

29. The apparatus as claimed in claim 21, wherein said power estimator (16) comprises:
   a decoder (35) for decoding filtered data as an address;
   a look-up table (36) addressed by said decoder (35) for containing squared values of said addresses;
   a summator (37) connected to said look-up table (36) for summing values consecutively rad out of said table (36);
   a scanner (38) controlling repetitive and consecutive addressing and summing said squared values by said summator (37);
   a third register file (39) connected to said summator (37) and having serial-in, parallel-out structure and containing new summed data in its upper register and the oldest data in its lowest register;
   a replacer (40) having a first input connected to the upper register of said third register file (39), a second input connected to the lower register of the register file, and a third input connected to a fourth register file (41), said replacer (40) being adapted for adding actual values at its first input to and subtracting actual values at its second input from the value received from said fourth register file (41);
   the fourth register file (41) being connected to an output of said replacer (40) and having a serial-in, parallel-out structure storing calculated power values and shifting its contents down step by step and having parallel outputs, the first of them connected to said third input of said replacer (40) and all inputs being connected to a peak detector (42) adapted to transfer contents of said microcontroller (6).

30. The apparatus as claimed in claim 29, wherein said second frequency selective power estimator unit (17) includes:
   a fifth register file (48) having a serial-in, parallel-out structure and storing input data ($d_i$) measured in a time window;
   a decoder (49) for decoding data ($d_i$) stored in the fifth register file (48) and designating corresponding words of a second look-up table (50) containing products according to the following formulae:

$$_i = d_i * \sin(2\pi f_b i / n_{wb}) * Ba(i);$$

$$_i \leq d_i * \cos(2\pi f_b i / n_{wb}) * Ba(i);$$

where $d_i$ is the ith data sampled and digitized from the unfiltered signal, $n_{wb}$ is the size of window in number of sample times, Ba(i) stands for the triangular correction function of a Bartlett window;
   a third look-up table (53) connected to summators (51) and (52) and containing squared values as words having a length equal to the word length of said summators (51,52);
   one of said summators (51) adapted for summing words of said second look-up table (50) designated by said decoder (49) to provide an intermediate sum $$S_v = \sum_{i=0}^{n_{wb}} V_i;$$

where $S_v$ is an intermediate sum and squaring this sum by using the third look-up table (53) for providing a squared intermediate sum of $S_v^2$;

the other summator (52) adapted for summing words of said second look-up table (50) designated by said decoder to provide a second intermediate sum $$S_w = \sum_{i=0}^{n_{wb}} W_i;$$

and for squaring this sum by using said third look-up table (53) for providing squared intermediate sum of $S_w^2$;

an adder (54) for adding squared intermediate sums for providing a power level at a second test frequency ($f_b$):

$$P_b = (S_v^2 + S_w^2)/n_{wb},$$

where $P_b$ is the power in the actual time window for the frequency ($f_b$);

a sixth register file (55) having a serial-in parallel-out structure and storing the last five sums of adder (54); and a second peak detector (56) for indicating peak values of said power ($P_b$).

31. The apparatus as claimed in claim 29, wherein said decoders (29, 32) and summator (34) are adapted to be turned in sleep mode to reduce power consumption when no heartbeat is expected.

* * * * *